(12) United States Patent
Fichot et al.

(10) Patent No.: US 8,586,563 B2
(45) Date of Patent: *Nov. 19, 2013

(54) NUTRITIONAL COMPOSITION CONTAINING OLIGOSACCHARIDE MIXTURE

(75) Inventors: Marie-Claire Fichot, Blonay (CH);
Norbert Sprenger, Savigny (CH);
Francois-Pierre Martin, Penthalaz (CH); Sunil Kochhar, Savigny (CH);
Serge Rezzi, Chatel St Denis (CH)

(73) Assignee: Nestec S.A., Vevey (CH)

( * ) Notice: Subject to any disclaimer, the term of this patent is extended or adjusted under 35 U.S.C. 154(b) by 301 days.

This patent is subject to a terminal disclaimer.

(21) Appl. No.: 13/003,467

(22) PCT Filed: Jun. 19, 2009

(86) PCT No.: PCT/EP2009/057656
§ 371 (c)(1),
(2), (4) Date: Jan. 10, 2011

(87) PCT Pub. No.: WO2010/003803
PCT Pub. Date: Jan. 14, 2010

(65) Prior Publication Data
US 2011/0110904 A1 May 12, 2011

(30) Foreign Application Priority Data
Jul. 8, 2008 (EP) .................................... 08159900

(51) Int. Cl.
*A61K 31/7008* (2006.01)
*A61K 31/702* (2006.01)
*A61K 35/74* (2006.01)

(52) U.S. Cl.
USPC .............................. 514/54; 514/61; 424/93.45

(58) Field of Classification Search
USPC .................................... 514/54, 61; 424/93.44
See application file for complete search history.

(56) References Cited

U.S. PATENT DOCUMENTS

2003/0129278 A1    7/2003   Stahl et al.

FOREIGN PATENT DOCUMENTS

| EP | 1776877 | 4/2007 |
|----|---------|--------|
| WO | 0033854 | 6/2000 |
| WO | 0142263 | 6/2001 |
| WO | 2004002495 | 1/2004 |

(Continued)

OTHER PUBLICATIONS

Gopal et al., "Oligosaccharides and glycoconjugates in bovine milk and colostrum," Brit J Nutrition 84(Suppl 1):S69-S74, 2000.*

(Continued)

*Primary Examiner* — Rosanne Kosson
(74) *Attorney, Agent, or Firm* — K&L Gates LLP

(57) ABSTRACT

A nutritional composition for administration to an infant which composition comprises, on a dry matter basis, from 2.5 to 15.0 wt % of an oligosaccharide mixture consisting of N-acetylated oligosaccharide(s), galacto-oligosaccharide(s) and sialylated oligosaccharide(s) with the proviso that the composition comprises at least 0.02 wt % of an N-acetylated oligosaccharide, at least 2.0 wt % of a galacto-oligosaccharide and at least 0.04 wt % of a sialylated oligosaccharide and that the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. The composition is useful for administration to an infant in the first six months of life to reduce the risk of obesity later in life.

11 Claims, 1 Drawing Sheet

(56) References Cited

FOREIGN PATENT DOCUMENTS

| WO | 2006091103 | 8/2006 |
| WO | 2007073192 | 6/2007 |
| WO | 2007090894 | 8/2007 |
| WO | 2007101675 | 9/2007 |
| WO | WO 2007101675 A1 * | 9/2007 |

OTHER PUBLICATIONS

Haschke et al., "Clinical trials prove the safety and efficacy of the probiotic strain Bifidobacterium Bb12 in follow-up formula and growing-up milks," Monatsschrift Kinderheilkunde Suppl 1-98:S26-S30, 1998.*

Thurl et al., "Quantification of Individual Oligosaccharide Compounds from Human Milk Using High-pH Anion-Exchange Chromatography," Analytical Biochemistry, vol. 235, Article No. 0113 (1996), pp. 202-206—XP2439151A.

Stettler et al., "Weight Gain in the First Week of Life and Overweight in Adulthood—A Cohort Study of European American Subjects Fed Infant Formula," vol. III, No. 15, Apr. 2005 pp. 1897-1903—XP002507042.

* cited by examiner

NUTRITIONAL COMPOSITION CONTAINING OLIGOSACCHARIDE MIXTURE

FIELD OF THE INVENTION

The invention relates to a nutritional composition such as an infant formula supplemented with an oligosaccharide mixture.

BACKGROUND OF THE INVENTION

The human colon is colonised with a wide range of bacteria that have both positive and negative effects on gut physiology as well as having other systemic influences. Predominant groups of bacteria found in the colon include bacteroides, bifidobacteria, eubacteria, clostridia and lactobacilli. The bacteria present have fluctuating activities in response to substrate availability, redox potential, pH, $O_2$ tension and distribution in the colon. In general intestinal bacteria can be divided into species that exert either potentially harmful or beneficial effects on the host. Pathogenic effects (which may be caused by clostridia or bacteroides, for example) include diarrhoea, infections, liver damage, carcinogenesis and intestinal putrefaction. Health-promoting effects may be caused by the inhibition of growth of harmful bacteria, stimulation of immune functions, improving digestion and absorption of essential nutrients and synthesis of vitamins. An increase in numbers and/or activities of bacterial groups (such as *Bifidobacterium* and *Lactobacillus*) that may have health promoting properties is desirable.

As far as infants specifically are concerned, immediately before birth, the gastro-intestinal tract of a baby is thought to be sterile. During the process of birth, it encounters bacteria from the digestive tract and skin of the mother and starts to become colonised. Large differences exist with respect to the composition of the gut microbiota in response to the infant's feeding. The faecal flora of breast-fed infants includes appreciable populations of Bifidobacteria with some *Lactobacillus* species, whereas formula-fed infants have more complex microbiota, with Bifidobacteria, Bacteroides, Clostridia and Streptococci all usually present. After weaning, a pattern of gut microbiota that resembles the adult pattern becomes established.

One approach to promote the numbers and/or activities of beneficial bacteria in the colon is the addition of prebiotics to foodstuffs. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are very resistant to enzymatic hydrolysis, indicating that these oligosaccharides may display essential functions not directly related to their calorific value.

Mother's milk is recommended for all infants. However, in some cases breast feeding is inadequate or unsuccessful for medical reasons or the mother chooses not to breast feed. Infant formulas have been developed for these situations. As the composition of human milk becomes better understood, it has also been proposed to add prebiotics to infant formula. Various infant formulas supplemented with prebiotics such as mixtures of fructooligosaccharides and galactooligosaccharides for example are commercially available. However, such mixtures approximate only roughly the mixture of oligosaccharides in human milk. Over 100 different oligosaccharide components have been detected in human milk some of which have not been so far detected in animal milks such as bovine milk at all or have been detected only in small quantities. Examples of classes of human milk oligosaccharide that are present in bovine milk and colostrum only in very small quantities or not at all are sialylated and fucosylated oligosaccharides.

US Patent Application No. 2003/0129278 describes an oligosaccharide mixture based on oligosaccharides produced from one or several animal milks which is characterized in that it comprises at least two oligosaccharide fractions which are each composed of at least two different oligosaccharides, with free lactose not pertaining thereto. The total spectrum of the oligosaccharides present in the oligosaccharide mixture differs from those present in the animal milk or animal milks from which the oligosaccharide fractions were extracted. Further a) if said oligosaccharides are extracted from only one animal milk, the proportion of neutral oligosaccharides to acidic (sialylated) oligosaccharides is 90-60: 10-40 weight %, or b) if said oligosaccharides are extracted from at least two animal milks, the oligosaccharides extracted from two different animal milks each make up 10 weight % of the total amount of oligosaccharides present in the oligosaccharide mixture.

WO2007/090894 describes an oligosaccharide mixture which comprises 5 to 70 wt % of at least one N-acetylated oligosaccharide, 20 to 90 wt % of at least one neutral galacto-oligosaccharide and 5 to 50 wt % of at least one sialylated oligosaccharide.

Most research interest has focused on the fermentability and bifidogenicity of oligosaccharide prebiotics. However, in vitro studies have shown that a number of oligosaccharide prebiotics mimic the eukaryotic cell surface receptors to which virulent bacteria adhere as part of the pathogenicity process (Shoaf et al, 2006). Further, trans-galacto-oligosaccharides have been found to enhance the protective abilities of *Bifidobacterium breve* in mice infected with *Salmonella enterica* (Asahara et al, 2001). Other potential benefits of prebiotics have also been investigated in adults including immunomodulatory properties, bone mineralisation and cardiovascular effects. Studies on neonates and infants have concentrated on the abilities of oligosaccharides to increase faecal Bifidobacteria populations. Surprisingly few studies have been carried out on disease prevention or possible treatment benefits of prebiotic use in infants.

In recent years, concerns about overweight and obesity in the adult population have grown substantially to the point where obesity is the most burdensome and costly nutritional condition worldwide. As a result, attention is starting to focus on the significance of developments during infancy for the risk of obesity later in life with particular regard to the extent to which growth during infancy may be a predictor of later adiposity. Some commentators believe that weight gain in the first six months of life is primarily a gain in fat; if weight gain in infancy is indeed predictive of later adiposity, it follows that gains in adiposity in infancy may need to be carefully monitored to reduce the risk of obesity of the individual later in life (Gilman M. W., "The first months of life: a critical period for development of obesity" Am J Clin Nutr 2008; 87: 1587-9).

SUMMARY OF THE INVENTION

The present inventors have surprisingly discovered that the administration of a mixture of prebiotic oligosaccharides comprising galacto-oligosaccharides with small quantities of more complex oligosaccharide species such as sialylated oligosaccharides and non-sialylated oligosaccharides including at least one N-acetyl group to germ-free mice inoculated with a human baby microbiota modulates lipid metabolism by reducing lipogenesis and promoting fatty acid beta-oxidation as compared with a control group not receiving the oligosaccharide mixture.

Accordingly, the present invention provides the use of an N-acetylated oligosaccharide, a galacto-oligosaccharide and a sialylated oligosaccharide in the manufacture of a nutritional composition for administration to an infant in the first six months of life to reduce the risk of obesity later in life.

The invention extends to a nutritional composition for administration to an infant which composition comprises, on a dry matter basis, from 2.5 to 15.0 wt % of an oligosaccharide mixture consisting of N-acetylated oligosaccharide(s), galacto-oligosaccharide(s) and sialylated oligosaccharide(s) with the proviso that the composition comprises at least 0.02 wt % of an N-acetylated oligosaccharide, at least 2.0 wt % of a galacto-oligosaccharide and at least 0.04 wt % of a sialylated oligosaccharide and that the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture.

The benefits of a nutritional composition according to the invention extend to reduction of lipogenesis and higher beta-oxidation of fatty acids.

In an embodiment the oligosaccharide mixture may be derived from animal milk, such as one or more of cows' milk, goats' milk or buffalo milk.

Preferably, the nutritional composition is an infant formula, but it may be any food or drink consumed by infants in the first few months of life including a therapeutic nutritional composition meeting the requirements of the EU regulations governing Foods for Special Medical Purposes (FSMP).

DETAILED DESCRIPTION OF THE INVENTION

Figure 1:
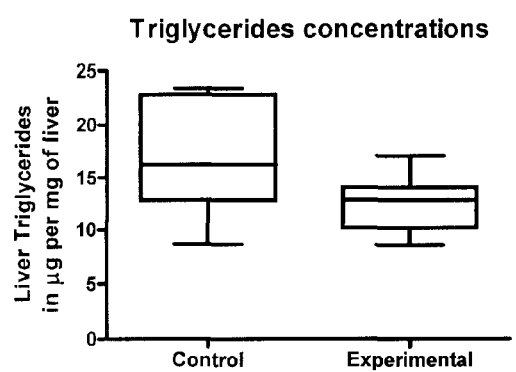
FIG. 1 shows a comparison of the concentrations of triglycerides in the livers of mice from the control group (n=9) and mice from the experimental group (n=10) displayed using box-and-whisker plots.

In this specification, the following expressions have the meanings assigned to them below:—

"galacto-oligosaccharide" means an oligosaccharide comprising two or more galactose molecules which has no charge and no N-acetyl residue;

"infant" means a child under the age of 12 months;

"infant formula" means a foodstuff intended for the complete nutrition of infants during the first four to six months of life. (Article 1.2 of the European Commission Directive 91/321/EEC of 14 May 1991 on infant formulae and follow-on formulae);

"N-acetylated oligosaccharide" means an oligosaccharide having an N-acetyl residue;

"oligosaccharide" means a carbohydrate having a degree of polymerisation (DP) ranging from 2 to 20 inclusive but not including lactose;

"prebiotic" means a selectively fermented ingredient that allows specific changes, both in the composition and/or activity in the gastrointestinal microbiota that confers benefits upon host well-being and health (Bouhnik et al, 2004);

"sialylated oligosaccharide" means an oligosaccharide having a sialic acid residue with associated charge.

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1,4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

Preferably, the nutritional composition comprises 3.0 to 12.0% of the oligosaccharide mixture, more preferably from 4.0 to 7.0% of the oligosaccharide mixture.

The nutritional composition preferably comprises at least 0.03 wt % of an N-acetylated oligosaccharide, at least 3.0 wt % of a galacto-oligosaccharide and at least 0.08 wt % of a sialylated oligosaccharide, more preferably at least 0.04 wt % of an N-acetylated oligosaccharide, at least 4.0 wt % of a galacto-oligosaccharide and at least 0.09 wt % of a sialylated oligosaccharide.

A nutritional composition according to the invention preferably also comprises at least one probiotic bacterial strain. A probiotic is a microbial cell preparation or components of microbial cells with a beneficial effect on the health or well-being of the host. Suitable probiotic bacterial strains include *Lactobacillus rhamnosus* ATCC 53103 obtainable from Valio Oy of Finland under the trade mark LGG, *Lactobacillus rhamnosus* CGMCC 1.3724, *Lactobacillus paracasei* CNCM I-2116, *Lactobacillus reuteri* ATCC 55730 and *Lactobacillus reuteri* DSM 17938 obtainable from Biogaia, *Lactobacillus fermentum* VRI 003, *Streptococcus salivarius* DSM 13084 sold by BLIS Technologies Limited of New Zealand under the designation K12, *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium infantis* sold by Procter & Gamble Co. under the trade mark Bifantis and the strain of *Bifidobacterium breve* sold by Institut Rosell (Lallemand) under the trade mark R0070. The probiotic may be added in an amount between 10e3 and 10e12 cfu/g powder, more preferably between 10e7 and 10e12 cfu/g powder.

Preferably the nutritional composition according to the invention is an infant formula. The general composition of an infant formula according to the invention will now be described by way of example.

The formula contains a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

An infant formula according to the present invention contains a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

An infant formula according to the present invention contains a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula will also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as lactoferrin, nucleotides, nucleosides, and the like.

Finally, the formula will contain from 2.5 to 15.0 wt % of an oligosaccharide mixture consisting of N-acetylated oligosaccharide(s), galacto-oligosaccharide(s) and sialylated oligosaccharide(s) in amounts of at least 0.02 wt % of an N-acetylated oligosaccharide, at least 2.0 wt % of a galacto-oligosaccharide and at least 0.04 wt % of a sialylated oligosaccharide, the N-acetylated oligosaccharide(s) comprising 0.5 to 4.0% of the oligosaccharide mixture, the galacto-oligosaccharide(s) comprising 92.0 to 98.5% of the oligosaccharide mixture and the sialylated oligosaccharide(s) comprising 1.0 to 4.0% of the oligosaccharide mixture.

The infant formula may be prepared by blending together the protein source, the carbohydrate source and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture is conveniently standardised at this point.

The homogenised mixture is transferred to a suitable drying apparatus, such as a spray drier or freeze drier, and converted to powder. The powder should have a moisture content of less than about 5% by weight.

The oligosaccharides may be added directly to the infant formula by dry mixing.

Preferably, the infant formula according to the invention is fed to the baby at every feed.

The invention will now be illustrated by reference to the following examples.

Example 1

An example of the composition of an infant formula according to the present invention is given below.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Galacto-oligosaccharides (g) | 1.1 | 6.8 |
| N-acetylated oligosaccharides (g) | 0.027 | 0.055 |
| Sialylated oligosaccharides (g) | 0.027 | 0.134 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

Example 2

The effect of a nutritional composition according to the invention on lipogenesis and fat oxidation was investigated in germ free mice inoculated with a human baby microbiota (HBM).

Experimental Design.

A total of 19 C3H female germ-free mice (Charles River, France) were housed under the same environmental conditions and were fed with a standard semi-synthetic irradiated rodent diet (Reeves et al, 1993). At 8 weeks of age, the germ-free mice received a single dose of human baby microbiota (HBM) bacteria mixture and were assigned randomly to 2 groups which followed different nutritional interventions over a 2 week period. The HBM composition was previously reported (Martin et al, 2007). One group was kept as control, and was fed with a 'basal mix' diet containing in composition 2.5% of a glucose-lactose mix (1.25% each) (control group, n=9). A second group of mice was fed with a diet containing 0.11% N-acetylated oligosaccharides, 2.7% galacto-oligosaccharides and 0.11% sialylated oligosaccharides (experimental group, n=10).

Sample Collection and Analytical Measures

Morning spot urines, blood plasma, and intact liver tissues were collected upon animal autopsy and snap-frozen prior to metabonomic analysis. Metabonomics using high resolution spectroscopic methods with subsequent multivariate statistical analyses is a well-established strategy for differential metabolic pathway profiling and assessment of dietary intervention effects and efficacy (Martin et al, 2008; Nicholson et al, 2005; Rezzi et al, 2007b; Rezzi et al, 2007a; Stella et al, 2006). The metabolic profiles were mined with multivariate analytical methods to recover metabolic probes of oligosaccharide intervention, which serve as reference for describing and predicting groups of animals according to treatments (Table 1).

Results

Figure 2:
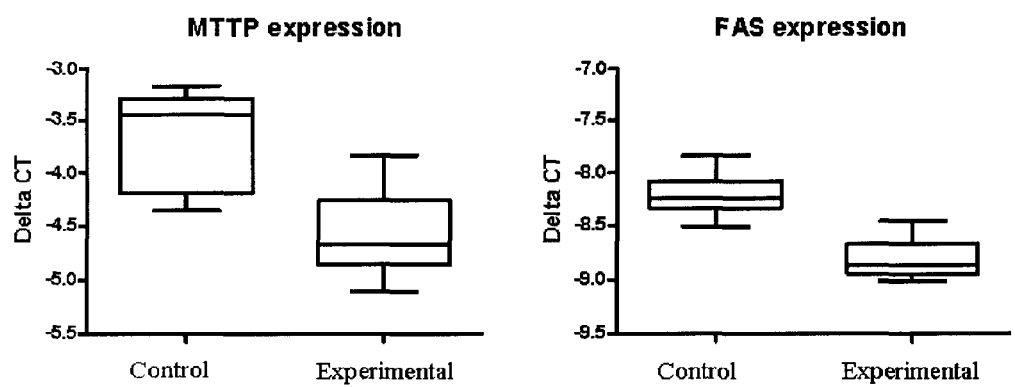
FIG. 2 shows a comparison of the expression of microsomal triglyceride transfer protein (MTTP) and fatty acid synthase (FAS) in the livers of mice from the control group (n=9) and the experimental group (n=10) displayed using box-and-whisker plots.

Table 1 and FIG. 1 show that use of a nutritional composition according to the invention reduced triglyceride concentration in the liver. The control and experimental groups were compared using unpaired Student's t-test and the difference was statistical significant at 95% confidence level. Table 1 and FIG. 2 show that use of a nutritional composition according to the invention also reduced lipogenesis and triacylglycerol incorporation into lipoproteins in the liver, the measure Delta CT plotted on the y-axis in FIG. 2 being the difference between the threshold cycle of the gene of interest and that of the endogenous reference gene. The decrease in expression levels in animals in the experimental group was significant at 99.9% confidence level when using unpaired Student's t-test. Higher urinary excretion of carnitine and acetyl-carnitine further showed enhancement of fatty acid oxidation (Table 1). These results together with higher betaine homocysteine methyl transferase metabolic activity in the liver (Table 1) indicated higher secretion of nascent lipoprotein particles, smaller in size and carrying less triacylglycerols.

Measures of triglycerides and activity of microsomal triglyceride transfer protein (MTTP) and fatty acid synthase (FAS) in the livers of mice in the control and experimental groups confirmed that mice in the experimental group had decreased hepatic triglycerides, lipogenic activities (FAS) and incorporation of triglycerides into lipoproteins (MTTP) (FIG. 2,).

The higher concentrations of carnitine and acetyl-carnitine and lower levels of L-aminoadipate and α-keto-isocaproate in urine of mice receiving prebiotic provide further evidence of a shift in lipid metabolism (Kliewer et al, 1997). In particular, carnitine is a well-characterized cofactor required for transformation of free long-chain fatty acids into acylcarnitines and their subsequent transport into the mitochondrial matrix, where they undergo β-oxidation (Bremer, 1983). Therefore, the results indicate enhancement of fatty acid oxidation (Table 1).

These results show liver-specific changes in betaine homocysteine methyl transferase (BHMT), metabolic pathways that closely interconnect choline, betaine and the formation of methionine from homocysteine (Niculescu & Zeisel, 2002). Increased expression of BHMT has been reported as a potential mechanism contributing to higher ApoB secretion available for VLDL assembly (Sparks et al, 2006). Moreover, previous studies described that certain complex carbohydrate (starch) diets result in higher secretion of nascent VLDL particles, smaller in size and carrying less triacylglycerols, and increased VLDL apo B fractional catabolic rates (Fernandez et al, 1996). Therefore, enhanced BHMT metabolism and lower MTTP activities indicate higher apo B apoproteins synthesis and decreased transfer of lipids into nascent lipoproteins, which suggests the involvement of a similar mechanism in response to this intervention.

TABLE 1

Influential metabolites describing prebiotic metabolic effects in plasma, liver and urine

| Metabolite | Control Group | Experimental Group |
|---|---|---|
| Plasma | | $Q_Y^2 = 29\%, R_X^2 = 86\%$ |
| Lipoproteins | 0.5 ± 0.2 | 0.4 ± 0.1 |
| Liver | | $Q_Y^2 = 36\%, R_X^2 = 46\%$ |
| Betaine | 1.6 ± 0.3 | 2.5 ± 0.2 *** |
| Choline | 0.5 ± 0.2 | 1.1 ± 0.2 *** |
| DMG | 0.06 ± 0.02 | 0.19 ± 0.05 *** |
| Triglycerides | 3.6 ± 1.3 | 2.1 ± 0.4 * |
| Phosphocholine | 1.7 ± 0.3 | 2.4 ± 0.3 *** |
| Sarcosine | 0.14 ± 0.03 | 0.18 ± 0.02 * |
| Urine | | $Q_Y^2 = 70\%, R_X^2 = 49\%$ |
| Carnitine | 0.3 ± 0.06 | 5.2 ± 1.3 *** |
| N-acetyl-carnitine | 0.17 ± 0.02 | 1.3 ± 0.3 *** |
| α-keto-isocaproate | 1.3 ± 0.3 | 0.9 ± 0.1 * |
| α-aminoadipate | 0.33 ± 0.05 | 0.19 ± 0.02 *** |

O-PLS models were generated with 1 predictive component, and 2 orthogonal components to discriminate between 2 groups of mice. The $R_X^2$ value shows how much of the variation in the dataset X is explained by the model. The $Q_Y^2$ value represents the predictability of the models, and relates to its statistical validity. Data are presented as area normalized intensities (a.u.) of representative metabolite signals as means ± standard deviation (SD). The values for the HBM mice supplemented with prebiotics were compared to HBM control mice, *, and *** designate significant difference at 95% and 99.9% confidence level, respectively.

The invention claimed is:

1. A nutritional composition for administration to an infant comprising, on a dry matter basis, from 2.5 to 15.0 wt % of an oligosaccharide mixture consisting of N-acetylated oligosaccharide(s), galacto-oligosaccharide(s) and sialylated oligosaccharide(s) wherein the composition comprises at least 0.02 wt % of an N-acetylated oligosaccharide, at least 2.0 wt % of a galacto-oligosaccharide and at least 0.04 wt % of a sialylated oligosaccharide and wherein the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture.

2. The composition of claim 1 comprising at least 0.03 wt % of an N-acetylated oligosaccharide, at least 3.0 wt % of a galacto-oligosaccharide and at least 0.08 wt % of a sialylated oligosaccharide.

3. The composition of claim 1, comprising at least 0.04 wt % of an N-acetylated oligosaccharide, at least 4.0 wt % of a galacto-oligosaccharide and at least 0.09 wt % of a sialylated oligosaccharide.

4. The composition of claim 1, comprising 3.0 to 12.0% of the oligosaccharide mixture.

5. The composition of claim 1, comprising 4.0 to 7.0% of the oligosaccharide mixture.

6. The composition of claim 1, wherein the N-acetylated oligosaccharide is selected from the group consisting of GalNAcα1-3Galβ1-4Glc; Galβ1-6GalNAcα1-3Galβ1-4Glc; and a mixture thereof.

7. The composition of claim 1, wherein the galacto-oligosaccharide is selected from the group consisting of Galβ1-6Gal; Galβ1-6Galβ1-4Glc; Galβ1-6Galβ1-6Glc; Galβ1-3Galβ1-3Glc; Galβ1-3Galβ1-4Glc; Galβ1-6Galβ1-6Galβ1-4Glc; Galβ1-6Galβ1-3Galβ1-4Glc; Galβ1-3Galβ1-6Galβ1-4Glc; Galβ1-3Galβ1-3Galβ1-4Glc; Galβ1-4Galβ1-4Glc; Galβ1-4Galβ1-4Galβ1-4Glc and mixtures thereof.

8. The composition of claim 1, wherein the sialylated oligosaccharide is selected from the group consisting of NeuAcα2-3Galβ1-4Glc; NeuAca2-6Galβ1-4Glc; and a mixture thereof.

9. The composition of claim 1, comprising a probiotic bacterial strain.

10. The composition of claim 9, wherein the probiotic bacterial strain is selected from the group consisting of *Lactobacillus rhamnosus* ATCC 53103, *Lactobacillus rhamnosus* CGMCC 1.3724, *Lactobacillus reuteri* DSM 17938, *Streptococcus salivarius* DSM 13084 and *Bifidobacterium lactis* CNCM I-3446.

11. The composition of claim 1 which is an infant formula.

* * * * *